United States Patent [19]

Horn et al.

[11] Patent Number: 4,948,366

[45] Date of Patent: Aug. 14, 1990

[54] ADHESIVE BOND STRENGTH CONTROL FOR ORTHODONTIC BRACKETS

[75] Inventors: Jerold S. Horn, Azusa; Henrick K. Gille, Monrovia, both of Calif.

[73] Assignee: Unitek Corporation, Monrovia, Calif.

[21] Appl. No.: 390,426

[22] Filed: Aug. 3, 1989

Related U.S. Application Data

[63] Continuation of Ser. No. 067,243, Jun. 26, 1987, abandoned.

[51] Int. Cl.$^5$ .......................... A01N 1/02; A61C 3/00
[52] U.S. Cl. ........................................ 433/9; 427/379; 428/429; 156/326; 433/8
[58] Field of Search .................. 433/8, 9, 217.1, 228.1; 428/429; 427/379; 525/342, 478

[56] References Cited

U.S. PATENT DOCUMENTS

| | | |
|---|---|---|
| 3,369,297 | 2/1968 | Halpern et al. . |
| 3,423,828 | 1/1969 | Halpern et al. . |
| 4,130,677 | 12/1978 | Heintsberger . |
| 4,144,376 | 3/1979 | Beckmann et al. . |
| 4,147,685 | 4/1979 | Smith .............................. 525/478 X |
| 4,181,687 | 1/1980 | Ward et al. ..................... 525/342 X |
| 4,242,413 | 12/1980 | Iwahashi et al. . |
| 4,247,354 | 1/1981 | Ward et al. ..................... 525/342 X |
| 4,294,349 | 10/1981 | Ibsen et al. . |
| 4,303,739 | 12/1981 | Beckmann et al. . |
| 4,315,970 | 2/1982 | McGee .................................. 428/412 |
| 4,364,731 | 12/1982 | Norling et al. ....................... 433/218 |
| 4,595,598 | 6/1986 | De Luca et al. ......................... 427/2 |
| 4,673,354 | 6/1987 | Culler ................................ 433/217.1 |
| 4,681,538 | 7/1987 | De Luca et al. . |
| 4,744,759 | 5/1988 | Bowen .............................. 433/228.1 |

OTHER PUBLICATIONS

Semmelman et al., "Silane Bonding Porcelain Teeth to Acrylic", pp. 69 to 73, *Jada*, vol. 76, Jan. 1968.

E. P. Plueddemann, "Aqueous Solutions of Silane Coupling Agents", pp. 49 to 73, Plenum Press, New York 1982.

Meyer R. Rosen, "From Treating Solution to Filler Surface and Beyond—The Life History of a Silane Coupling Agent", Technological Review, Journal of Coatings Technology, pp. 70 to 82, 1978.

"Union Carbide Silane Adhesion Promoters in Glass Reinforced Thermosetting Resin Systems", Union Carbide Silane Adhesion Promoters, Union Carbide Corporation, 15 pages, Jun. 1968.

"Filler TReatment", Union Carbide adhesion Promotors, Union Carbide Corporation, 29 pages, Dec. 1968.

"Silane Adhesion Promoters in Mineral-Filled Composites", Union Carbide Adhesion Promoters, Union Carbide Corporation, 40 pages, Jun. 1973.

"Organofunctional Silanes—A Profile" Union Carbide Corporation, 45 pages, May 1981.

*Primary Examiner*—V. Millin
*Attorney, Agent, or Firm*—Donald M. Sell; Walter N. Kirn; James D. Christoff

[57] ABSTRACT

Ceramic orthodontic brackets are bonded to teeth with dental adhesive. Each bracket has a silica-containing layer on the tooth facing base of the bracket. A silanation layer is also applied to the base. The silanation layer is deposited from a solution containing a first silane coupling agent reactive with organic resin in the adhesive and a second silane coupling agent having a non-reactive orgainc group. Collectively the silanes occupy all of the silanation sites on the silica-containing substrate. By controlling the ratio of reactive and non-reactive silane coupling agents, the bond strength between the substrate and the adhesive can be controlled. A set of ceramic orthodontic brackets can have uniform force of removal by varying the porportions of silane coupling agents on the brackets.

47 Claims, 2 Drawing Sheets

ADHESIVE BOND STRENGTH CONTROL FOR ORTHODONTIC BRACKETS

This is a continuatiuon division of aplication Ser. No. 67,243 filed June 26, 1987 now abandoned.

BACKGROUND OF THE INVENTION

This invention relates to control of adhesive bond strength where a silane coupling agent is used to promote adhesion, and is particularly applicable for bonding ceramic brackets to teeth for orthodontic braces.

A recent development in the field of orthodontic appliances provides transparent or translucent ceramic brackets for adhesive bonding to teeth. An arch wire is secured to such brackets in a conventional manner for making orthodontic adjustments. Such a ceramic bracket is particularly advantageous since it has outstanding mechanical strength and is cosmetically acceptable since the underlying tooth color shows through the bracket.

Such brackets may be made of single crystal or polycrystalline aluminum oxide for superior optical and mechanical properties. It can, however, be difficult to bond aluminum oxide adhesively to the surface of a tooth since adhesion between aluminum oxide and acceptable dental adhesives is relatively low. Therefore, a layer of high silica ceramic such as a layer of glass can be provided on the base of the bracket, that is, the surface to be bonded to the tooth. The silica containing surface is then "primed" or "silanated" with a conventional silane coupling agent. An exemplary silane coupling agent comprises gamma-methacryloxypropyl trimethoxysilane. Conventional acrylic and methacrylic resin dental adhesives bond strongly to such a silane-treated surface and form a secure bond to the face of the tooth.

It is desirable to provide a technique that provides adhesion with a strength that is subject to easy control. It is also desirable that such a technique be applicable to adhesive bonding of other substrates.

BRIEF SUMMARY OF THE INVENTION

There is, therefore, provided in practice of this invention according to a presently preferred embodiment, a method for controlling bond strength between an inorganic substrate and an organic adhesive. The inorganic substrate is contacted with a composition comprising a mixture of an organofunctional silane coupling agent which is reactive with an organic resin and an organosilane coupling agent which is not reactive with the organic resin. When the organic resin is used to form an adhesive bond, for example, it reacts with the organofunctional composition in proportion to presence of the functional silane coupling agent on the substrate. This enables production of a set of orthodontic brackets with approximately the same removal force from teeth by variation of the proportions of reactive and nonreactive silane coupling agents on the bases of the brackets in the set.

BRIEF DESCRIPTION OF THE DRAWINGS

These and other features and advantages of the present invention will be appreciated as the same becomes better understood by reference to the following detailed description when considered in connection with the accompanying drawings wherein.

DETAILED DESCRIPTION

Figure 1:
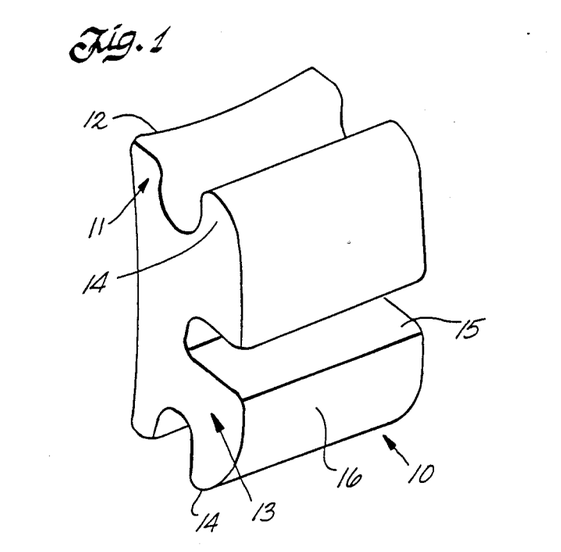
FIG. 1 is a pictorial schematic view of an orthodontic bracket.

FIG. 1 shows an exemplary orthodontic appliance in the form of an orthodontic bracket 10. The bracket has a base 11 suitable for direct bonding to a tooth. The tooth facing surface 12 of the base is preferably concavely curved in a conventional manner about both a mesiodistal axis and an apical axis to match the natural convexity of the tooth labial surface. Other curvatures can be used to accommodate lingual bracket positioning.

A bracket body 13 extends from the base 11 to define bracket tie wings 14 for ligature anchorage and a mesiodistally oriented arch wire slot 15 extending from an outer body surface 16 into the bracket body. The presence or absence of tie wings and their specific structure is not a feature of the invention, and the base and arch wire slot may be angulated as desired to minimize or eliminate torquing or other bends of the arch wire. It should be understood that the orthodontic bracket illustrated is FIG. 1 is largely schematic and it merely indicates a context in which this invention is applicable. A number of such brackets shaped to fit individual teeth are commonly used in sets for orthodontic adjustments.

A preferred orthodontic appliance is formed of high density translucent polycrystalline aluminum oxide. This material is preferred because of its high strength and optical characteristics. If desired, this invention may be used with other ceramic orthodontic brackets such as ones made of single crystal alumina, porcelain, or with metal brackets.

Figure 2:
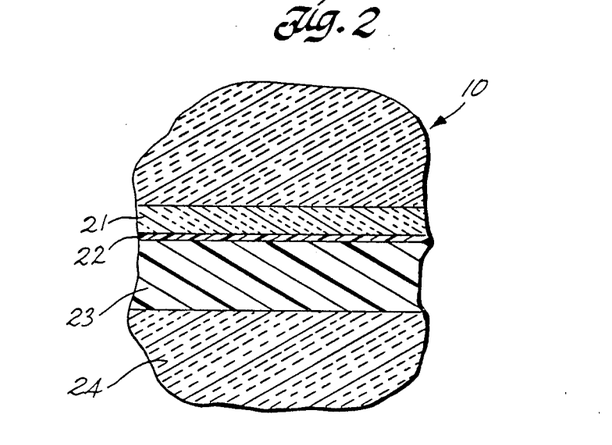
FIG. 2 is a fragmentary cross section of the adhesive bond between such a bracket and a tooth.

In a preferred embodiment the tooth facing surface 12 of the bracket receives a silica-containing coating. This silicious coating may be applied in the form of a thin layer of glass frit which is then melted to adhere to the alumina. Other techniques may also be used for applying a silica-containing coating to the alumina substrate, such as vapor or vacuum deposition, sputtering, ion bombardment or the like. The method for applying a silica coating can be conventional and forms no part of this invention. A preferred embodiment, however, has a silica-containing layer 21 on the base of the bracket 10.

A silanation layer 22 deposited from liquid silane coupling agents is applied to the silica layer. The application of the silane coupling agent layer 22 is described in greater detail hereinafter. In effect, the coupling agent layer changes the characteristics of the surface from the inorganic silica of the base layer to an organic moiety of the silane coupling agent.

As used herein, the term silane coupling agent is used in a generic sense. It refers to an organosilane such as gamma-methacryloxypropyltrimethoxysilane or to the hydrolyzed equivalent thereof such as a silanol where the methoxy groups have been hydrolyzed to hydroxyl groups. It may also refer to the deposition product after such a silane or silanol has condensed on a substrate to form a condensation polymer, as well as reacting with silicious or like silane-reactive sites on the substrate. Thus, as used herein, silane coupling agent may refer to a silane, a silanol, or a condensation product thereof.

After silanation, an adhesive 23 is applied to the base of the bracket for adhering it to the face of a tooth 24.

A conventional acrylic or methacrylic dental adhesive is preferred. The dental adhesive may be applied to the silane coupling agent layer by the dentist immediately before the bracket is placed on the tooth. Acrylic and methacrylic adhesives are preferred since they are strong, stable in the oral environment, and cure quite rapidly for minimizing the time the patient must spend in the chair. A number of such adhesives are commercially available, mostly based on methacrylate resins with various fillers and the like. Amino acid or protein compositions referred to as barnacle glues and cyanoacrylates may also be employed.

A broad variety of organofunctional silanes are commercially available as coupling agents. Broadly speaking, the organosilanes have one to three hydrolyzable moieties and three to one non-hydrolyzable organic groups on a silicon atom. Most commonly the hydrolyzable moieties comprise chlorine, a siloxy group or an alkoxy group. Alkoxy groups are preferred in practice of this invention since the hydrolysis products are alcohols. A broad variety of organic groups may be included on the silane molecule to provide desired properties of the coupling agent.

In use, a hydrolyzable "end" of the organosilane interacts with a solid substrate, and if more than one hydrolyzable group is present, may also condense with available hydrolyzable groups of neighboring silane molecules to form a strong, adherent layer. Particularly strong bonds are formed between an organosilane and a silica-containing substrate. A number of theories have been propounded for the interaction between the silane coupling agent and various substrates. A detailed understanding of these is not necessary for practice of this invention. It is hypothesized that there are a limited number of sites on the silica which can react with the silane coupling agent. It is desirable that substantially all of these sites react with silane coupling agents in practice of this invention.

The organic group of the silane coupling agent interacts with organic resins to give greater adhesion between the resin and the silane coupling agent than is typically possible between the resin and a substrate, absent such silanation. Often polymerization between the organic resin and the non-hydrolyzable organic group of the silane coupling agent will provide the strongest bonds; for example, a silane coupling agent having a methacryl group can polymerize with a methacrylate resin and gives particularly strong bonding. Some silane coupling agents having non-copolymerizable organic groups may also provide higher adhesion to a resin than obtained between a non-silanated inorganic substrate and the resin.

A particularly preferred organofunctional silane for use with dental adhesives comprises gamma-methacryloxypropyltrimethoxysilane. This material is available from Union Carbide Corporation under their designation A-174, from Dow Corning Corporation under their designation Z6030, from Petrarch Systems Silanes & Silicones, Bristol, Pa., under their designation M8550, or from PCR Research Chemicals, Inc., under their designation 29670-7. Many other silane coupling agents are commercially available, some of which have organic groups having various degrees of reactivity and others of which are not reactive, insofar as reaction with a specific organic resin is concerned. Additional exemplary silane coupling agents from the many available include 3-(2-Aminoethylamino)propyltrimethoxysilane
3-Chloropropyltrichlorosilane
3-Chloropropyltrimethoxysilane
Dimethyldichlorosilane
Ethyltrichlorosilane
Methyltrichlorosilane
Methyltrimethoxysilane
Phenylmethyldichlorosilane
Phenyltrichlorosilane
Trimethylchlorosilane
Vinyltriacetoxysilane
(2-methoxyethoxy)silane
Vinyl-tris(2-methoxyethoxy)silane
Beta-3,(4-epoxycyclohexyl)ethyltrimethoxysilane
Gamma-mercaptopropyltrimethoxysilane
Gamma-aminopropyltriethoxysilane Silane coupling agents may be applied to a substrate without hydrolysis or may be prehydrolyzed before being applied to the substrate. If the silane is applied to the surface without hydrolysis, it is typically first dissolved in anhydrous organic solvent to a dilution to give a desired quantity of the silane coupling agent on the surface after evaporation of the solvent. In such an embodiment, the silane coupling agent cures in air due to presence of adventitious water and may form strong bonds with the solid substrate. Heating the silanated surface can accelerate such curing.

It is generally considered that better adhesion of the organosilane to the substrate is obtained by prehydrolyzing the silane. For example, with the preferred organosilane, the methoxy groups are hydrolyzed to hydroxyl groups in the solution before application to the solid substrate. Such prehydrolysis can be obtained in a solution of alcohol and water acidified with suitable acid, for example acetic acid. Such a solution is formulated and permitted to stand for a sufficient period to substantially completely hydrolyze the silane before it is used. Such solutions are typically used within a reasonable period after formulation. Alumina brackets have been adhered to teeth or test substrates by applying a silica-containing layer on the base of the bracket and silanating the bracket with prehydroyzed gamma-methacryloxypropyltrimethoxysilane. The silanated surface is then adhesively bonded to the tooth or other substrate using a methacrylate adhesive such as DYNA-BOND PLUS from Unitek Corporation, Monrovia, Calif.

Surprisingly, it is sometimes a problem that the adhesive bond to the tooth has too high a strength. Eventually an orthodontic bracket must be removed from the tooth when treatment is completed. The bracket is typically removed by gripping with a suitable instrument and twisting the bracket so that the adhesive is caused to fail in rotational shear. With a strong adhesive, removal forces may traumatize tender teeth sensitized by a regimen of orthodontic adjustment, causing undesirable discomfort to the patient.

It is, therefore, desirable to provide an adhesive bond between a bracket and tooth which has controlled strength so that the forces required for removal are minimized to minimize trauma to the teeth. The strength required can differ for different teeth and different brackets to yield the same removal force for all brackets in a set.

Preferably, the average force required to remove brackets in a standardized test described hereinafter, is in the range of from 35 to 40 pounds (16 to 18 kg.). The average force for removal should be more than about 20 pounds (9 kg.) to resist the forces of orthodontic adjustment and occlusal forces superimposed thereon. It is also desirable that the average removal force be less than about 65 pounds (30 kg.) to avoid trauma to the teeth when the bracket is removed.

With prior techniques, removal forces appreciably more than 65 pounds (30 kg.) may be encountered, particularly when non-standard removal techniques are employed. This is deemed to be too high a removal force for at least some ceramic brackets adhesively bonded to teeth. This invention provides a technique for controlling the bond strength between the bracket and tooth so that the removal force has a desired value.

In the preferred embodiment, gamma-methacryloxypropyltrimethoxysilane coupling agent reacts with the methacrylate resin in a dental adhesive, thereby forming a particularly strong bond. The bond strength between the silane coupling agent and the adhesive is therefore reduced by employing a mixture of the organofunctional gamma-methacryloxypropyl .trimethoxysilane and an organosilane coupling agent which includes an organic group which does not react with the methacrylate resin. In a macroscopic sense, the effect is to reduce the bond strength in proportion to the dilution of the organofunctional component with a nonfunctional component. A suitable non-reactive organosilane comprises n-propyltrimethoxysilane. Other suitable relatively non-reactive materials include propyltriethoxysilane, 3-methoxypropyltrimethoxysilane, ethyltriethoxysilane, phenyltriethoxysilane, methyltriethoxysilane, dimethyldiethoxysilane, ethyltrimethoxysilane, ethyltriacetoxysilane, ethyltrichlorosilane, phenyltrimethoxysilane and phenethyltrimethoxysilane. Such materials are available from commercial silane suppliers such as those listed above. A number of other organosilane coupling agents are suitable, particularly when the organic groups thereon do not react with the organic resin of the adhesive. Such a suitable material may be reactive in the context of a different adhesive resin, but may be essentially inactive in the context of a suitable dental adhesive. Alkyl non-reactive groups are attractive since they are not reactive with conventional adhesives and are less expensive than more exotic silanes.

It is desirable that the reactive group and the end of the non-reactive group on the silane coupling agent be sufficiently separated from the hydrolyzable groups that there is little influence on the hydrolysis or condensation reactions. This promotes equivalent reactivity of both the reactive and non-reactive silane coupling agent with the substrate. Preferably the separation is provided by a carbon chain having at least three carbon atoms. It is particularly desirable that the non-reactive silane coupling agent comprise n-propyltrimethoxysilane or other silane with at least three carbon atoms in the non-reactive organic group. The preferred gamma-methacryloxypropyltrimethoxysilane has a three carbon atom propyl chain between the reactive group and the silicon atom. It appears that this length of carbon chain is sufficient to isolate the hydrolyzable portion of the silane from any significant influence of the active group. A similar effect may be obtained with an aryl ring separated from the silicon atom by a shorter carbon chain. Thus, a suitable material is phenethyltrimethoxysilane.

It is desirable that the hydrolyzable groups of the organosilanes used in the mixture be similar. This is to assure that the reactivity of the silanes as they hydrolyze is equivalent. Although it is preferred that the hydrolyzable groups on the silane coupling agent are the same for the coupling agents used in the mixture, it will be apparent that this desideratum is of diminished significance when the silanes are prehydrolyzed before contact with the solid substrate. The hydrolysis, in effect, makes the silane coupling agents equivalent insofar as reaction with the substrate is concerned.

There are only a finite number of silanation sites on the substrate, that is, the silica-containing layer on the base of the orthodontic bracket. Assuming that a reactive silane coupling agent such as gamma-methacryloxypropyltrimethoxysilane interacts with all of the available sites, the maximum bond strength available should be obtained. If the number of sites for reaction with the adhesive are reduced, the average bond strength can also be reduced proportionately. This is accomplished by interacting a portion of the coupling sites on the silica containing substrate with a silane coupling agent that does not react with the methacrylate adhesive, for example, n-propyltrimethoxysilane. By supplanting the reactive silane coupling agent with a proportion of nonreactive silane coupling agent which has equivalent bonding to the substrate, closer control of the bond strength can be obtained then by merely diluting the proportion of the reactive silane coupling agent in a solution. In effect, a portion of the bonding sites on the substrate are disabled from combining with the reactive silane coupling agent. A desired bond strength, and hence removal force, can be readily provided by varying the ratio of higher strength, reactive silane coupling agent, and lower strength, nonreactive silane coupling agent.

It is common to provide sets of orthodontic brackets for use on teeth ranging from incisors to bicuspids. Such sets have orthodontic brackets of different sizes and angular relations between the arch wire slot and the base, and with different curvatures on the base. A representative set of brackets comprises twenty brackets. For the upper teeth, there are brackets for the centrals, laterals, cuspids and bicuspids. In the lower half of the set, there are brackets for the lower anteriors, cuspids and bicuspids. If desired, ceramic brackets can be provided for molars, however, it is more common to employ a buccal tube for orthodontic adjustment or anchorage involving the molars. Since molars do not ordinarily show, the cosmetic advantages of a ceramic molar bracket are not as significant.

In practice of this invention the strength of the adhesive bond provided on each of the brackets in such a set can be controlled to a desired value to provide adequate strength for orthodontic adjustment, yet low enough strength that the brackets can be removed without trauma to the teeth.

When such brackets in a set are adhesively bonded to their respective teeth without practice of this invention, the force required to remove the brackets from their respective teeth can vary appreciably. The force required to remove brackets from the bicuspids is high because of the substantial curvature of these teeth. Forces are next highest for the cuspids for similar reasons. Forces are still lower for the upper centrals and laterals which are relatively flat. The most easily removed are the lower anteriors since they generally have a smaller area bonded to the tooth. Also, for reasons not fully understood, it is found that the apparent bond strength per unit area of small brackets is generally larger than the apparent bond strength per unit area of large brackets.

It is desirable that the force required to remove each of the brackets in a set be approximately the same. Thus, it is desirable that the strength of the bond between the base of the bracket and the adhesive be inversely proportional to the force required to remove the brackets in the absence of differences due to practice of this invention. For example, a relatively higher bond strength may be employed on brackets for mounting on lower anteriors than would be employed for brackets mounted on cuspids or bicuspids. Generally speaking, trauma to the tooth is more likely on the relatively more curved surfaces of the cuspids and bicuspids than the somewhat flatter surfaces of the upper centrals and laterals.

Thus, a set of dental brackets can be provided with two or three or more different values of controlled bond strength, depending on whether the brackets are to be mounted on the upper centrals, laterals, cuspids, bicuspids or lower anteriors, and depending on the size of each bracket. Since this control is provided at the stage of manufacturing where the silane coupling agent is applied to the substrate, it is essentially taken out of the hands of the orthodontist who can then use the same adhesive for all of the brackets in a set and still obtain appropriate bond strengths.

With techniques as provided in practice of this invention, sets of brackets can be made with any desired relation between the removal forces for the several brackets in a set. The sequence of bond strengths mentioned above is but one example, presently preferred for general application, of such a combination of removal forces.

The effect of substituting a nonreactive organosilane coupling agent for a portion of the organofunctional silane coupling agent is demonstrated in a series of tests wherein the bases of orthodontic brackets were silanated using differing proportions of gamma-methacryloxypropyltrimethoxysilane and n-propyltrimethoxysilane. In a series of tests upper central orthodontic brackets fabricated of polycrystalline aluminum oxide were used. The base of each bracket was previously coated with a thin layer of silica-containing glass applied as a frit and melted onto the alumina. So far as it is known all of the brackets used in the tests were identical. Each bracket had a base 0.13 by 0.14 inch (3.3 by 3.6 mm.).

Each of the brackets was silanated by dipping the bracket into one of the prehydrolyzed silane solutions described below and drying in air at 100° C for 1½ hours.

Each of five test solutions was prepared by mixing 180 grams of ethyl alcohol with 20 grams of deionized water. Ten grams of the selected silane mixture was mixed into this solution and acetic acid was added with stirring until the pH was no more than 4. The solution was permitted to stand at room temperature for at least two hours to permit complete hydrolysis of the silane or silanes in the solution. At the end of each day any excess solution was discarded, and fresh solution was made daily.

The silane coupling agents used were Silane A174 from Union Carbide, which is gamma-methacryloxypropyltrimethoxysilane, and Petrach P0810, which is n-propyltrimethoxysilane. In all cases the silanes were premixed before adding to the alcohol and water mixture. In solution one, the silane added to the solution was 100% A174. In solution two, there was a 50/50 molar ratio of A174 to P0810. In solution three, there was a molar ratio of 40/60 or A174 to P0810. In solution four, there was a molar ratio of 30/70 of A174 to P0810. In solution five, there was a molar ratio of 25/75 of A174 to P0810.

Twenty brackets were silanated with each of these test solutions. In addition, twenty brackets with no silanation treatment were tested (a molar ratio of 0/0).

In a pull test for bond strength or removal force, each of the brackets was adhesively bonded to the exterior of a ring cut from ¾ inch, schedule 40, polyvinylchloride pipe cleaned with isopropyl alcohol and acetone. The ring surface was primed with UNITE No-Mix primer from Unitek Corporation. The ring surface was then primed with a mixture of equal parts of DYNA-BOND PLUS base and catalyst primer from Unitek Corporation.

Equal parts of DYNA-BOND PLUS base and catalyst adhesive pastes where mixed and promptly applied to the bonding surface of each test bracket so that a slight excess of the adhesive covered the entire bonding surface. Each bracket was immediately placed on the ring with tweezers and pressed in its center to set the bracket firmly against the ring surface and squeeze out excess adhesive. The brackets were oriented on the ring with the gingival and occlusal directions parallel to the ring axis and the distal and mesial directions tangential to the ring. After bonding, the brackets were held for at least 16 hours at room temperature before pull testing.

In the pull test the ring is mounted on the lower jaw of an Instron testing machine with the axis of the ring aligned toward the upper jaw. A 0.016 inch (0.4 mm.) diameter wire descending from the upper jaws is looped under the bracket's occlusal tie wings. This applies a load more or less parallel to the bonding surface so that there is a large component of shear on the adhesive bond, with a small component of "peeling," thereby simulating occlusal forces. The wire is pulled at a rate of 0.2 inches (5 mm.) per minute with a full scale on the testing machine of 100 lbs (45 kg). The bond strength at separation of the bracket from the ring is recorded.

For each silane coupling agent solution, twenty brackets were silanated, adhesively bonded to a ring, and pull tested. An additional twenty brackets were bonded and tested without any silanation. The average bond strength or removal force for the twenty specimens in each group is set forth in the following table.

| Test Solution | | Average Bond |
|---|---|---|
| | Mole Percent | |
| No. | A174 | P0180 | Strength (lbs) |
| 1 | 100 | 0 | 70 |
| 2 | 50 | 50 | 64 |
| 3 | 40 | 60 | 54 |
| 4 | 30 | 70 | 37 |
| 5 | 25 | 75 | 40 |
| | 0 | 0 | 13 |

Figure 3:
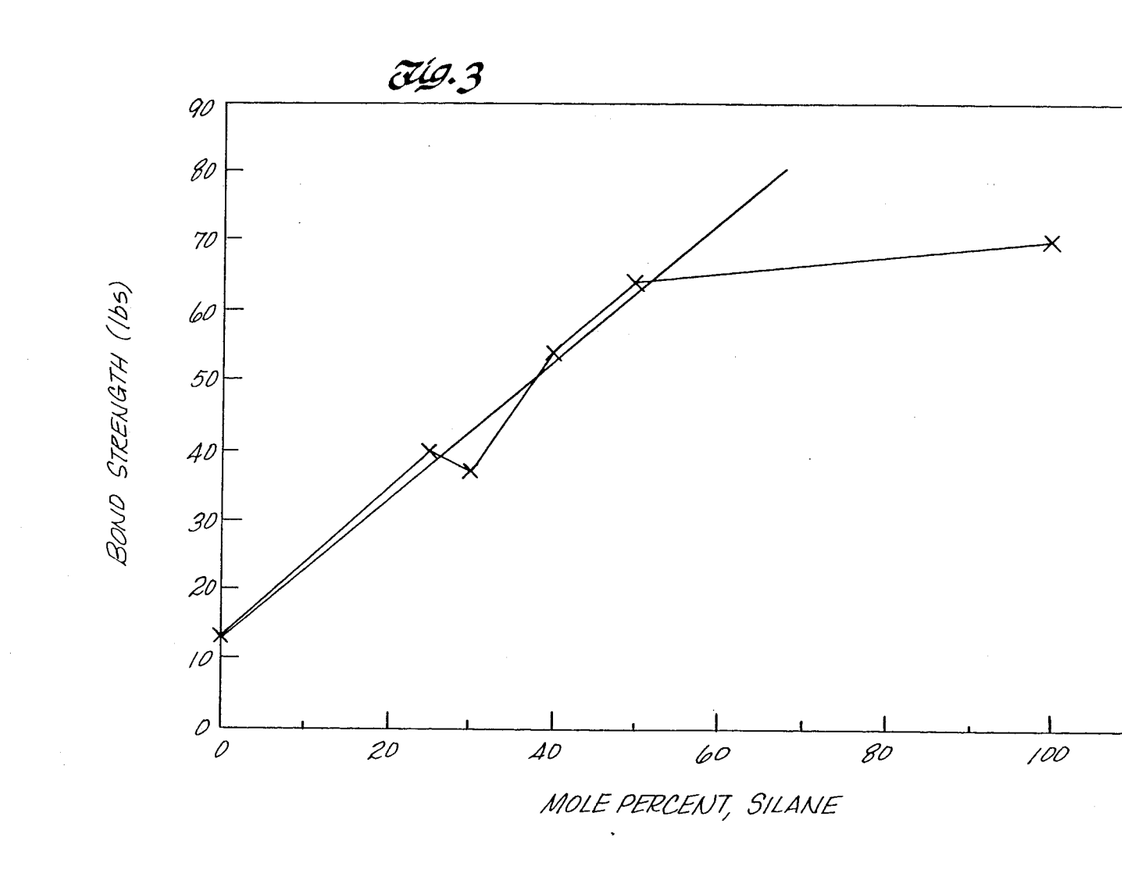
FIG. 3 is a graph of bond strength as a function of the proportion of reactive silane coupling agent.

These data are also plotted in FIG. 3, showing bond strength as a function of the mole percentage of A174 in the solution. It will be recognized that the test with 0 mole percent A174 had no silanation of the base by any silane coupling agent. FIG. 3 also includes a straight line which is a least squares fit of the bond strength as a function of mole percentage of A174 from 0 to 50 mole percent. In the least squares fit the correlation coefficient (R) is 0.87.

These data show that by occupying the available silanation sites on the substrate with a mixture of organosilane coupling agents, one of which has organic groups which react with the methacrylate resin adhesive and one of which has organic groups which do not react with the methacrylate adhesive, the bond strength can be controlled to give sufficient bond strength to withstand orthodontic adjustment and occlusal forces, while trauma to the tooth is minimized.

Although described in the context of adhesive bonding of ceramic orthodontic brackets to teeth, it will be apparent that principles of this invention are applicable in other contexts. A broad variety of situations require organic resin bonding to articles having an inorganic substrate. It is often desirable to silanate those substrates to promote better adhesion. A broad variety of silane coupling agents are available for applications involving a variety of organic resins which may be employed in adhesives, sealants, or structural assemblages.

For example, silanes having vinyl groups are suitable as "primers" for polyesters. Exemplary vinyl silane coupling agents include vinyl-trichlorosilane, vinyltriethoxysilane, vinyl-trimethoxysilane, vinyl-tris-(beta-methoxyethoxy)silane and vinyltriacetoxysilane. If desired, one may use gamma-ureidoalkyltriethoxysilane for compatibility with urea formaldehyde resins. Aminoalkyl silanes such as gamma-aminopropyltriethoxysilane, gamma-aminopropyltrimethoxysilane, N-beta-(aminoethyl)-gamma-aminopropyltrimethoxysilane and N'-(beta-aminoethyl)-N-(beta-amino-ethyl)-gamma-aminopropyltrimethoxysilane may be used for a broad variety of resins including phenolics, vinyls, polyurethanes, epoxys and acrylics. Mercaptoalkyl silane coupling agents may be used with epoxy resins or polysulfides. Exemplary materials include gamma-mercaptopropyltrimethoxysilane and gamma-mercaptopropyltriethoxysilane. A broad variety of essentially nonreactive organosilanes are commercially available for mixing with such reactive organosilanes for control of bond strength in such contexts. Other examples will be appreciated where silane coupling agents are employed for enhancing adhesion between an inorganic substrate, particularly a silica containing inorganic substrate, and an organic resin.

It will, therefore, be appreciated that within the scope of the appended claims the invention may be practiced otherwise than as specifically described.

We claim:

1. A method for controlling bond strength between an inorganic substrate and an acrylate or methacrylate resin comprising the steps of:
   contacting the inorganic substrate with a composition comprising a mixture of an organofunctional silane coupling agent comprising a methacryl group which is reactive with the resin and an organosilane coupling agent which is not reactive with the resin; and
   reacting the resin with the organofunctional silane coupling agent on the substrate for providing an average bond strength less than the bond strength obtained when only the silane coupling agent comprising a methacryl group is applied to the base of such a substrate.

2. A method as recited in claim 1 wherein the organofunctnional silane coupling agent and the organosilane coupling agent have the same hydrolyzable moieties.

3. A method as recited in claim 1 wherein the organofunctional silane coupling agent comprises gamma-methacryloxypropyltrimethoxysilane and the nonfunctional organosilane coupling agent comprises n-propyltrimethoxysilane.

4. A method as recited in claim 1 wherein the silane coupling agents are prehydrolyzed before contacting the inorganic substrate.

5. A method for controlling bond strength between a silica-containing substrate and an organic resin comprising the step of contacting the silica-containing substrate with a composition comprising an organofunctional silane coupling agent which is reactive with the organic resin and diluted with sufficient organosilane coupling agent which is not reactive with the organic resin to reduce the average bond strength between the substrate and the organic resin to a selected fraction of the bond strength obtained using only the organofunctional silane.

6. A method as recited in claim 5 wherein the silane coupling agents are prehydrolyzed before contacting the silica-containing substrate.

7. A method as recited in claim 5 wherein the organic resin comprises an acrylate or methacrylate resin and the organofunctional silane coupling agent comprises a methacryl group.

8. A method as recited in claim 5 wherein each of the silanes comprises hydrolyzable alkoxy groups.

9. A method as recited in claim 8 wherein the silanes are prehydrolyzed before contacting the silica-containing substrate.

10. A method for controlling bond strength between a dental substrate and a dental adhesive comprising the steps of:
    contacting the dental substrate with a composition comprising a mixture of a first silane coupling agent comprising methacryl groups which has a relatively higher bond strength with the dental adhesive and a second silane coupling agent having at least three carbon atoms which has a relatively lower bond strength with the dental adhesive; and
    contacting the dental adhesive and the silane coupling agents on the substrate for providing a bond strength intermediate between the bond strength of either silane coupling agent above.

11. A method as recited in claim 10 wherein the reactive silane coupling agent comprises gamma-methacryloxypropyltrimethoxysilane and the nonreactive organosilane coupling agent comprises n-propyltrimethoxysilane.

12. A method for bonding an orthodontic bracket to a tooth comprising the steps of:
    applying to the base of the bracket a solution containing a mixture of silane coupling agents, at least one of the silane coupling agents comprising a methacryl group and at least one of the silane coupling agents comprising an organic group which is not reactive with a methacrylate resin;
    condensing the coupling agents on the substrate; and
    bonding the bracket to a tooth with an adhesive including a methacrylate resin for providing an average bond strength less than the bond strength obtained when only the silane coupling agent comprising a methacryl group is applied to the base of such a bracket.

13. A method as recited in claim 12 comprising prehydrolyzing the silanes int eh solution before applying the solution to the base of the bracket.

14. A method as recited in claim 12 wherein the organic group which is not reactive with a methacrylate resin comprises an organic group having at least three carbon atoms.

15. A method as recited in claim 12 wherein each of the silanes has substantially equal reactivity with the base of the bracket.

16. A method as edited in claim 12 further comprising applying a silica-containing layer on the base of the bracket before applying the solution.

17. A method as recited in claim 12 wherein the methacryl-containing silane coupling agent comprises gamma-methacryloxypropyltrimethoxysilane or the hydrolyzed equivalent thereof, and the nonreactive orgaosilane coupling agent comprises n-propyltrimethoxysilane or the hydrolyzed equivalent thereof.

18. A method for bonding a ceramic orthodontic bracket to a tooth comprising the steps of:
applying a silica-containing layer on the base of the ceramic bracket;
silanating the silica-containing layer with a mixture of silane coupling agents, at least one of the silane coupling agents comprising a methacryl group which is reactive with a methacrylate dental adhesive and at least one of the silane coupling agents comprising an organic group which is not reactive with a methacrylate dental adhesive; and
bonding the bracket to a tooth with a methacrylate dental adhesive for providing sufficient adhesive bond strength for orthodontic adjustment and insufficient to avoid trauma to the tooth upon removal.

19. A method as recited in claim 18 wherein the silanes are prehydrolyzed before silanating the silica-containing layer.

20. A method as recited in claim 18 wherein the silane comprising a methacryl group comprises gamma-methacryloxypropyltrimethoxysilane or the hydrolyzed equivalent thereof.

21. A method as recited in claim 20 wherein the nonreactive silane coupling agent comprises n-propyltrimethoxysilane.

22. A method as recited in claim 18 wherein each of the silanes has substantially equal reactivity with the silica-containing layer.

23. A method as recited in claim 18 wherein the adhesive bond strength is in the range of from 20 to 65 pounds.

24. A method as recited in claim 18 wherein the adhesive bond strength is in the range of from 35 to 40 pounds.

25. An orthodontic bracket comprising:
a ceramic body;
a silica-containing layer on the base of the body; and
a silane coupling agent layer on the silica-containing base, the silane coupling agent layer comprising a mixture of organic groups which are reactive with a methacrylate adhesive and organic groups which are not reactive with the methacrylate adhesive.

26. An orthodontic bracket as recited in claim 25 wherein the organofunctional groups comprise methacryl groups.

27. An orthodontic bracket as recited in claim 26 wherein the non-reactive organic groups have at least three carbon atoms.

28. An orthodontic bracket as recited in claim 25 wherein the reactive organic groups comprise gamma-methacryloxypropyl groups and the nonreactive groups comprise n-propyl groups.

29. An orthodontic bracket comprising:
a ceramic body; and
a silica-containing layer on the base of the ceramic body; and characterized by
substantially all of the silanation sites on the silica-containing layer being occupied by silane coupling agents, a first portion of the silane coupling agents having a higher bonding strength to a dental adhesive, and a second portion of the silane coupling agents having a lower bonding strength to a dental adhesive for obtaining a bonding strength intermediate between the bonding strength of either silane coupling agent alone.

30. An orthodontic bracket as recited in claim 29 wherein the portion of silane coupling agents having a higher strength comprises organic groups reactive with a dental adhesive.

31. An orthodontic bracket as recited in claim 29 wherein the portion of silane coupling agents having a higher strength comprises methacryl groups.

32. An orthodontic bracket as recited in claim 31 wherein the second portion of silane coupling agents having a lower strength comprises organic groups having at least three carbon atoms.

33. An orthodontic bracket as recited in claim 29 wherein the first portion of silane coupling agents having a higher strength comprise gamma-methacryloxypropyl groups and the second portion of silane coupling agents having a lower strength comprise n-propyl groups.

34. A method as recited in claim 29 wherein the adhesive bond strength is in the range of from 20 to 65 pounds.

35. A method as recited in claim 29 wherein the adhesive bond strength is in the range of from 35 to 40 pounds.

36. A set of ceramic orthodontic brackets comprising:
lower anterior brackets;
central and lateral brackets;
cuspid brackets; and optionally
bicuspid brackets; and wherein
each bracket comprises a silanation layer on the base, such a silanation layer comprising a mixture of silane coupling agents, a first portion of the silane coupling agents having a higher bond strength to a dental adhesive and a second portion of the silane coupling agents having a lower bond strength to a dental adhesive, the proportion of the higher bond strength silane coupling agent to the lower bond strength coupling agent differing on the brackets for providing substantially the same removal force for each bracket in the set when debonded from its respective tooth.

37. A set of ceramic orthodontic brackets as recited in claim 36 wherein the proportion of the relatively higher bond strength silane coupling agent is greater in the silanation layer on the lower anterior brackets than the proportion of the higher bond strength silane coupling agent in the silanation layer on the bicuspid brackets.

38. A set of ceramic orthodontic brackets as recited in claim 36 wherein the proportion of higher bond strength silane coupling agent in the silanation layer on the central and lateral brackets is between the proportions of higher bond strength silane coupling agent on the lower anterior brackets and the bicuspid brackets.

39. A set of ceramic orthodontic brackets as recited in claim 36 wherein the removal force for each bracket in the set, when bonded to each respective tooth by a dental adhesive, is in the range of from 35 to 40 pounds.

40. An orthodontic bracket as recited in claim 36 wherein the portion of silane coupling agents having a higher strength comprises organic groups reactive with a dental adhesive.

41. An orthodontic bracket as recited in claim 36 wherein the first portion of silane coupling agents having a higher strength comprises methacryl groups.

42. A set of ceramic orthodontic brackets as recited in claim 36 wherein the higher bond strength coupling agent comprises gamma-methacryloxypropyl groups and the lower bond strength coupling agent comprises n-propyl groups.

43. A set of ceramic orthodontic brackets as recited in claim 36 wherein the removal force for each bracket in the set, when bonded to each respective tooth by a dental adhesive, is in the range of from 20 to 65 pounds.

44. A set of ceramic orthodontic brackets comprising:
central and lateral brackets having a silanation layer on the base thereof comprising a mixture of a first silane coupling agent having an organic group reactive with a dental adhesive and a second silane coupling agent having an organic group that is not reactive with a dental adhesive; and
cuspid and bicuspid brackets having a silanation layer on the base thereof comprising a mixture of the first silane coupling agent and the second silane coupling agent; and wherein
the ratio of the first silane coupling agent to the second silane coupling agent is greater on the central and lateral brackets than the ratio of the first silane coupling agent to the second silane coupling agent on the cuspid and bicuspid brackets.

45. A set of ceramic orthodontic brackets as recited in claim 44 further comprising lower anterior brackets having a silanation layer on the base thereof comprising a mixture of the first silane coupling agent and the second silane coupling agent, and wherein the ratio of the first silane coupling agent to the second silane coupling agent is greater on the lower anterior brackets than the ratio of the first silane coupling agent to the second silane coupling agent on the central and lateral brackets.

46. A set of ceramic orthodontic brackets as recited in claim 45 wherein the first silane coupling agent comprises methacryl groups.

47. A set of ceramic orthodontic brackets as recited in claim 44 wherein the second silane coupling agent comprises organic groups having at least three carbon atoms.

* * * * *

UNITED STATES PATENT AND TRADEMARK OFFICE
CERTIFICATE OF CORRECTION

PATENT NO. : 4,948,366
DATED : August 14, 1990
INVENTOR(S) : Jerold S. Horn and Henrick K. Gille It is certified that error appears in the above-identified patent and that said Letters Patent is hereby corrected as shown below:

Col. 1, line 5 - Change "division of aplication" to
-- of application --.

Col. 4, line 11 - Delete (2-methoxyethoxy)silane

Col. 10, line 65 - Change "int eh" to -- in the --.

Signed and Sealed this

Fifth Day of May, 1992

Attest:

DOUGLAS B. COMER

*Attesting Officer*   *Acting Commissioner of Patents and Trademarks*